(12) United States Patent
Reise et al.

(10) Patent No.: US 6,367,307 B1
(45) Date of Patent: Apr. 9, 2002

(54) CALIBRATED STOP BOLT FOR LONGITUDINAL SHOCK TEST FIXTURE

(75) Inventors: Christa M. Reise, Portsmouth, RI (US); James C. Butts, Casco, ME (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/267,916

(22) Filed: Mar. 2, 1999

(51) Int. Cl.[7] .............................. G01N 3/30; G01N 3/32; G01N 7/00; G01P 15/00
(52) U.S. Cl. ..................................... 73/12.01
(58) Field of Search ................ 73/12, 12.01, 11.07; 525/918; 114/238; 29/452

(56) References Cited

U.S. PATENT DOCUMENTS

| | | | | |
|---|---|---|---|---|
| 5,025,744 A | * | 6/1991 | Moody | 114/238 |
| 5,174,236 A | * | 12/1992 | Moody | 114/238 |
| 5,551,279 A | * | 9/1996 | Quick | 73/12.01 |
| 5,690,044 A | * | 11/1997 | Quick | 114/238 |
| 5,770,791 A | * | 6/1998 | Manahan, Sr. | 73/12.01 |

* cited by examiner

Primary Examiner—Benjamin R. Fuller
Assistant Examiner—Octavia Davis
(74) Attorney, Agent, or Firm—Michael J. Mcgowan; James M. Kasischke; Prithvi C. Lall

(57) ABSTRACT

A calibrated stop bolt is provided for measuring the dynamic load transmitted to the calibrated stop bolt during a shock test. The stop bolt includes an anterior extension and a posterior extension, for restraining a torpedo bearing plate therebetween, and also includes a plurality of strain gauges mounted at the top portion of each extension. In one embodiment, eight strain gauges are utilized, with two strain gauges placed on each side of the two extensions, i.e., in a full bridge arrangement. The calibrated stop bolt is preferably mounted to a base plate and bolted at each end to a longitudinal test fixture. The calibrated stop bolt can be utilized with a conventional longitudinal shock test fixture, torpedo shape and heavy weight shock machine.

18 Claims, 3 Drawing Sheets

US 6,367,307 B1

CALIBRATED STOP BOLT FOR LONGITUDINAL SHOCK TEST FIXTURE

STATEMENT OF GOVERNMENT INTEREST

The invention described herein may be manufactured by or for the Government of the United States of America for governmental purposes without the payment of any royalties thereon or therefor.

BACKGROUND OF THE INVENTION

(1) Field of the Invention

This invention relates generally to a simulated stop bolt, and more particularly to a calibrated stop bolt including a plurality of strain gauges for accurately measuring the dynamic load applied to the calibrated stop bolt during a shock test.

(2) Description of the Prior Art

Most work to date in torpedo tube shock improvement has centered on variations in the bearing plate and stop bolt designs. However, such modifications are often difficult to implement due to the limited information available on the dynamic loads transmitted to the submarine stop bolt. More particularly, current load limits for submarine stop bolts have been determined from static load tests. These values are conservative for high frequency shock events where higher material strengths are often encountered. This results in the difficulty of implementing modifications since the shock energy must be dissipated, and the load transmitted to the submarine stop bolt is limited, based upon values determined by static testing alone.

Shock test fixtures utilized in conjunction with a heavy-weight shock machine are the primary method for testing the effectiveness of torpedo bearing plate designs. In conventional shock testing, the torpedo bearing plate is restrained by a dummy or simulated stop bolt which acts as an interface between the torpedo bearing plate and the shock test fixture to prevent relative motion between the torpedo and the fixture. An example of such a conventional system is shown in FIG. 1, which is a cross-sectional side view of a simulated stop bolt 110, torpedo bearing plate 116 and longitudinal test fixture 126. Stop bolt 110 includes two extensions 114a, 114b which fit through two corresponding holes in the longitudinal test fixture 126, thereby restraining the bearing plate 116 on torpedo 119. By restraining movement of the bearing plate, relative motion between the torpedo and the shock test fixture is prevented. However, conventional longitudinal shock test fixtures are unable to measure the dynamic load transmitted to the simulated stop bolt, thus limiting the ability to improve bearing plate designs.

There is therefore needed an improved simulated stop bolt for shock testing which is capable of measuring the dynamic load transmitted to the simulated stop bolt, so that improvements in the design of torpedo bearing plates and submarine stop bolts can be implemented.

SUMMARY OF THE INVENTION

This invention provides a calibrated stop bolt for measuring the dynamic load transmitted to the calibrated stop bolt during a shock test. The stop bolt includes an anterior extension and a posterior extension, for restraining a torpedo bearing plate therebetween, and also includes a plurality of strain gauges mounted at the top portion of each extension. In one embodiment, eight strain gauges are utilized, with two strain gauges placed on each side of the two extensions, i.e., in a full bridge arrangement. The full bridge arrangement is the preferred arrangement because it doubles the rated sensitivity of a single strain gauge. The calibrated stop bolt is preferably mounted to a base plate and bolted at each end to a longitudinal test fixture. The calibrated stop bolt can be utilized with a conventional longitudinal shock test fixture, torpedo shape and heavy weight shock machine, as are known to those of skill in the art.

During a shock test, the bearing plate and calibrated stop bolt engage alternately at the interface between the bearing plate and the anterior and posterior stop bolt extensions, respectively. When the bearing plate and stop bolt engage, the strain gauges measure the strain at each location of the gauges. These strains can then be related to the load experienced at the interface of the bearing plate and the anterior stop bolt extension, and the interface of the bearing plate and the posterior stop bolt extension, so as to determine the dynamic load transmitted to the stop bolt during the shock test. The measurements taken during the shock test may be recorded, for example on a digital recording device, an analogue tape, or computer disc, in order to utilize the measurements in other, subsequent analysis.

It is therefore an object of the present invention to provide a calibrated stop bolt having a plurality of strain gauges mounted thereto for measuring the strain experienced by the calibrated stop bolt.

It is another object of the present invention to provide a calibrated stop bolt capable of measuring the dynamic load transmitted to the calibrated stop bolt during a shock test in order to prove that bearing plate modifications are in compliance with submarine interface requirements.

BRIEF DESCRIPTION OF THE DRAWINGS

The invention will be described with reference to the appended drawings, wherein common features of the invention are identified with common reference numerals in the multiple views provided of the invention and wherein.

DESCRIPTION OF THE PREFERRED EMBODIMENT

Figure 3:
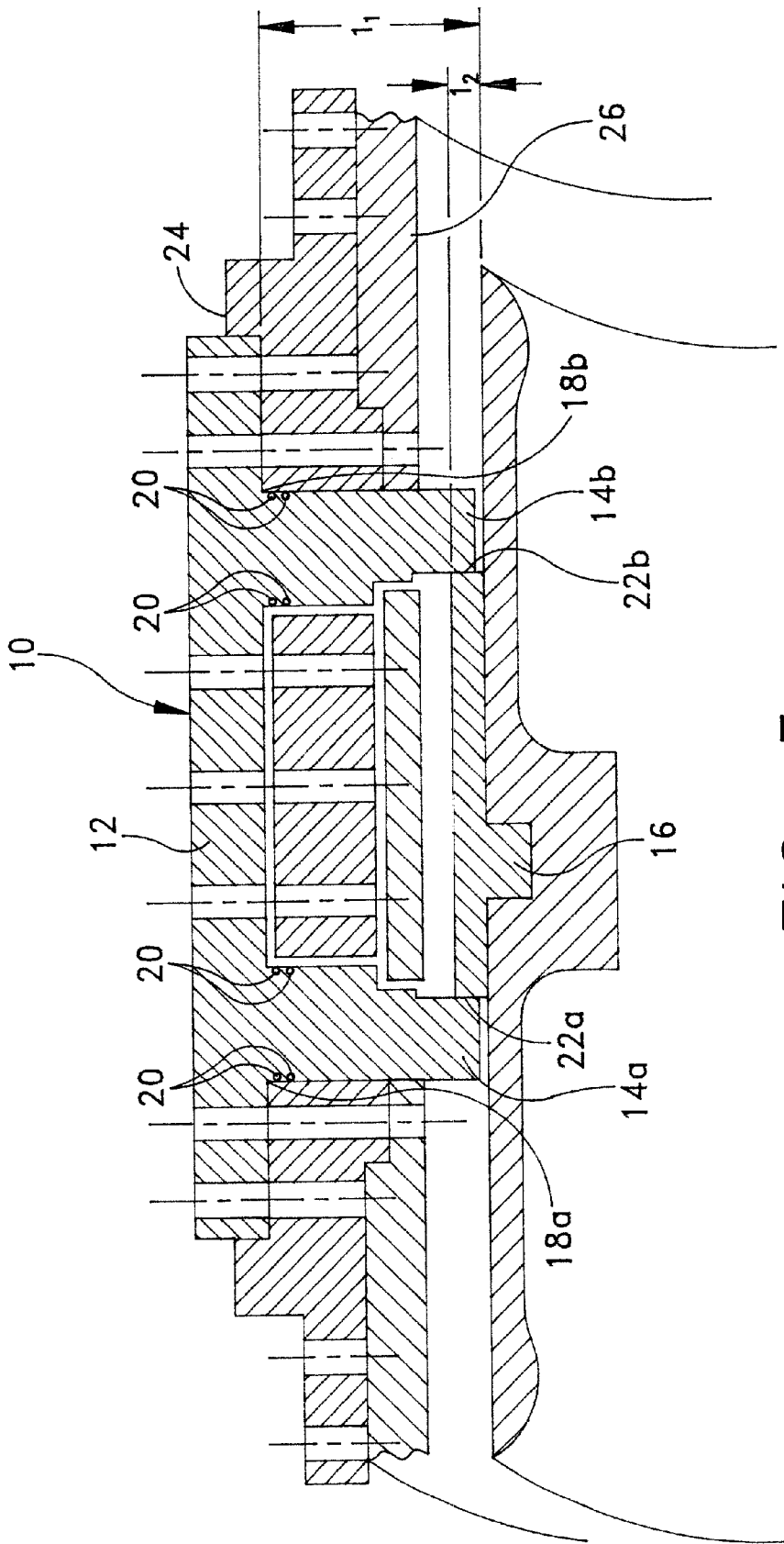
FIG. 3 is a cross-sectional side view of a calibrated stop bolt assembly according to the present invention which may be utilized in conjunction with the longitudinal shock test fixture, torpedo shape and heavy weight shock machine of FIG. 2.

The calibrated stop bolt assembly of the present invention is illustrated most clearly in FIG. 3. As will hereinafter be more fully described, the general basis for the invention is for strain gauges to measure the strains on a calibrated stop bolt during shock testing. The measured strain can then be related to the load experienced at the interface of a bearing plate and an anterior stop bolt extension, and the interface of the bearing plate and a posterior stop bolt extension, so as to determine the dynamic load transmitted to the calibrated stop bolt during the shock test.

The calibrated stop bolt 10 of the present invention includes a body member 12, an anterior extension 14a and a posterior extension 14b, extending from body member 12, for restraining torpedo bearing plate 16 therebetween. Mounted at a top portion 18a, 18b of the anterior and posterior extension 14a, 14b, respectively, are strain gauges 20. The strain gauges are preferably mounted as close to the top portion of each extension as possible, without causing the extensions to bend during shock testing. The strain gauges 20 are utilized to measure the strain at the interface or engagement area 22a, 22b between torpedo bearing plate 16 and the anterior and posterior extensions 14a, 14b of the stop bolt 10. Accurate dynamic load measurement is primarily a function of the length of the stop bolt extensions 14a, 14b relative to the expected variation in the length of the bearing plate engagement area 22a, 22b. In the present embodiment, the length ($l_1$) of the anterior and posterior extensions is preferably between about 2–3 inches, and is most preferably about 2.5 inches; while the length of the engagement area ($l_2$) may preferably vary between about 0.26 and 0.36 inches. For an extension length of about 2.5 inches and bearing plate engagement length of between 0.26 and 0.36 inches, the arrangement results in load measuring accuracy of +/–3%. Other lengths may be utilized for the extension and bearing plate engagement, however, the above values were chosen to maximize accuracy while lowering root stresses to an acceptable level. For example, although longer length extensions may be utilized to further increase the accuracy of the measurements, increasing the length of the extensions also increases bending stresses at the top of the extensions which may prove unacceptable by causing the extensions to bend during testing.

The strain gauges are preferably mounted in a full bridge arrangement, so as to accurately measure the strain placed on the stop bolt at the interface between the anterior and posterior extensions and the bearing plate. In a preferred embodiment, eight strain gauges are utilized, with two strain gauges placed on either side of the top portion of the anterior and the posterior extensions, i.e., in a full bridge arrangement as shown in FIG. 3. The full bridge arrangement is preferred because it doubles the rated sensitivity of a single stain gauge. Other numbers of strain gauges may be utilized, although at least four gauges should preferably be provided so that a strain gauge is mounted on either side of the top portion of both the anterior and the posterior extensions. The strain gauges may preferably have a gauge factor of 2.050 at 24° C., be ⅛" long, with a 120 Ohm resistance, such strain gauges being available from Micromeasurements Group, Inc. as style EA-062AP-120, or alternately, other conventional strain gauges as would be known to those skilled in the art may be utilized.

The stop bolt is preferably fabricated from a high strength material which will not deform during testing. The stop bolt is particularly susceptible to deformation at the interface with the bearing plate and at the top portion of the extensions. It is also preferred that the material utilized be corrosion resistant, since corrosion would interfere with the operation of the strain gauges. In the present embodiment 17-4PH stainless steel which was heat treated to H900 condition was utilized, although other materials of similar strength and corrosion resistance may be utilized, as would be known to those skilled in the art.

Figure 1:
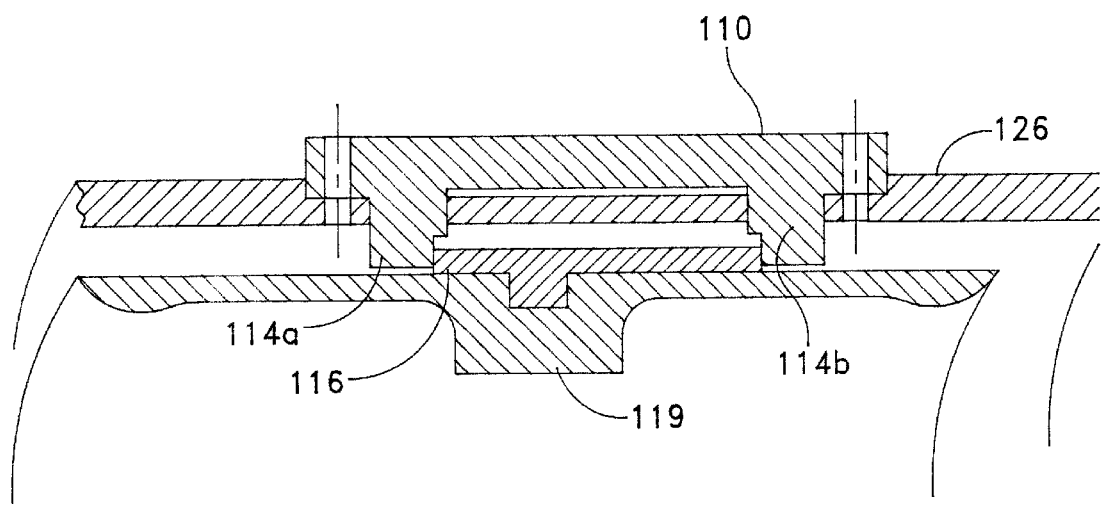
FIG. 1 is a cross-sectional side view of a longitudinal test fixture, a torpedo bearing plate and conventional stop bolt.
Figure 2:
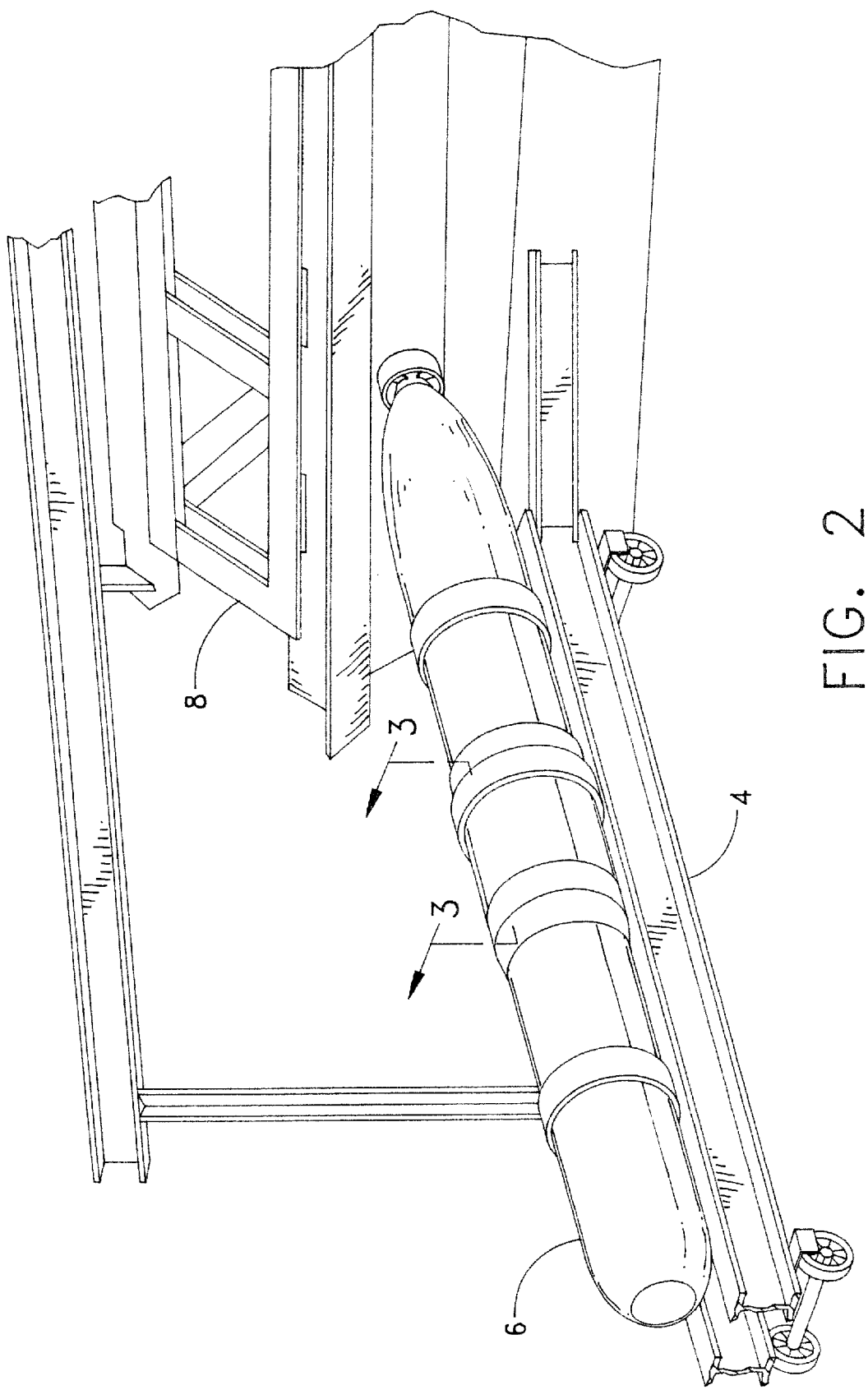
FIG. 2 is a perspective view of a longitudinal shock test fixture, torpedo shape, and heavy weight shock machine.

Prior to testing, the calibrated stop bolt 10 is mounted in a base plate 24 and bolted at each end to a longitudinal test fixture 26. In a preferred embodiment, the base plate 24 is disposed between body member 12 and the longitudinal test fixture 26. The calibrated stop bolt 10 can be utilized with a conventional longitudinal shock test fixture 4, torpedo shape 6 and heavy weight shock machine 8 as shown in FIG. 2.

The operation of the calibrated stop bolt 10 of the present invention will now be described. During a shock test performed according to known procedures, the bearing plate 16 and calibrated stop bolt 10 engage alternately at the interface 22a, b of the bearing plate 16 and the anterior and posterior stop bolt extensions, 14a, b respectively. When the bearing plate and stop bolt engage, the strain gauges measure the strain at each location of the gauges. These strains can then be related to the load experienced at the interface of the bearing plate and the anterior stop bolt extension, and the interface of the bearing plate and the posterior stop bolt extension, so as to determine the dynamic load transmitted to the stop bolt during the shock test. The dynamic load may then be utilized to prove that bearing plate modifications are in compliance with submarine interface requirements. The measurements taken during the shock test may be recorded, for example on a digital recording device, analogue tape or computer disc, in order to utilize the measurements in other, subsequent analysis.

While there is shown and described herein certain specific structure embodying the invention, it will be manifest to those skilled in the art that various modifications and rearrangements of the parts may be made without departing from the spirit and scope of the underlying inventive concept. For example, the material utilized for the stop bolt assembly and the number (more or less) and location of the strain gauges may be varied by one of skill in the art. Therefore, the invention is not limited to the particular forms shown and described herein, except insofar as indicated by the scope of the appended claims.

What is claimed is:

1. A calibrated stop bolt for determining a dynamic load applied to the stop bolt during a shock test, comprising:

a body member constructed and arranged to be secured to a test fixture such that the body member remains substantially stationary during the shock test;

an anterior extension and a posterior extension extending from the body member and each including a bottom portion constructed and arranged to restrain a torpedo bearing plate therebetween, the anterior and posterior extensions each further including a top portion opposite the bottom portion and adjacent the body member; and at least two strain gauges mounted to the top portion of both the anterior and posterior extensions, the strain gauges for measuring strain applied to the calibrated stop bolt at the interface of the bearing plate and the extensions during the shock test, wherein the measurements taken from the strain gauges are utilized to determine the dynamic load applied to the stop bolt during the shock test.

2. The calibrated stop bolt according to claim 1, wherein the strain gauges are mounted at the top portion of both the anterior and posterior extensions.

3. The calibrated stop bolt according to claim 2, wherein the strain gauges are mounted in a full bridge arrangement.

4. The calibrated stop bolt according to claim 2, wherein four strain gauges are mounted at the top portion of both the anterior and posterior extensions.

5. A method of measuring strain applied to a calibrated stop bolt comprising the steps of:

providing the stop bolt with a body member constructed and arranged to be secured to a test fixture such that the body member remains substantially stationary during the shock test, an anterior extension and a posterior extension each including a bottom portion constructed and arranged to restrain a torpedo bearing plate therebetween and a top portion opposite the bottom portion and adjacent the body member;

mounting at least two strain gauges to the top portion of both the anterior and posterior extensions;

mounting the stop bolt to a test fixture;

placing a torpedo bearing plate between the anterior and posterior extensions;

alternatively engaging the bearing plate and the calibrated stop bolt between an interface of the anterior extension and the bearing plate and the posterior extension and the bearing plate; and measuring the strain at each location of the strain gauges.

6. The method of measuring strain according to claim 5, further comprising the step of relating the measured strains to a load experienced at the interface of the anterior extension and the bearing plate and the posterior extension and the bearing plate so as to determine a dynamic load transmitted to the stop bolt.

7. The method of measuring dynamic load according to claim 5, further comprising the step of mounting the at least two strain gauges to a top portion of both the anterior and posterior extensions, adjacent the body member.

8. The method of measuring dynamic load according to claim 5, further comprising the step of mounting the at least two strain gauges in a full bridge arrangement.

9. The method of measuring dynamic load according to claim 5, wherein four strain gauges are mounted at the top portion of both the anterior and posterior extensions.

10. An apparatus for measuring alternating bending moments applied during a shock test, comprising:

a stop bolt having a body member constructed and arranged to be secured to a test fixture such that the body member remains substantially stationary during the shock test, an anterior extension and a posterior extension, both extensions extending from the body member, each extension having opposed forward and rear faces, the extensions constructed and arranged to restrain a torpedo bearing plate between the forward face of the posterior extension and the rear face of the anterior extension and at a distance from the body member of the stop bolt; and a pair of strain gauges mounted to each face of both the anterior and posterior extensions at a top portion of the extensions adjacent the body member, the strain gauges for measuring strain within the extensions during the shock test, wherein the measurements taken from the strain gauges are utilized to determine the alternating bending moments applied to the stop bolt.

11. The apparatus of claim 10, wherein the extensions have a total length of about 2.5 inches and a length contacting the bearing plate of about 0.26 to about 0.36 inches.

12. The apparatus of claim 10 wherein the strain gauges are mounted in full bridge arrangement.

13. The apparatus of claim 11 wherein the strain gauges are mounted in full bridge arrangement.

14. The calibrated stop bolt according to claim 1 wherein the anterior and posterior extensions are received through openings in the test fixture.

15. The calibrated stop bolt according to claim 1 further comprising a base plate disposed between the body member and the test fixture.

16. The calibrated stop bolt according to claim 15 wherein the base plate has openings formed therein corresponding to openings formed in the test fixture and the anterior and posterior extensions are received through the openings in both the base plate and test fixture.

17. The method of measuring dynamic load according to claim 5 further comprising the step of mounting the calibrated stop bolt to a base plate disposed between the body member of the stop bolt and the test fixture.

18. The apparatus of claim 10 further comprising a base plate secured to the stop bolt and capable of being secured to the test fixture between the test fixture and the stop bolt.

* * * * *